United States Patent
Jang

(10) Patent No.: US 10,215,121 B2
(45) Date of Patent: Feb. 26, 2019

(54) METHOD AND APPARATUS FOR HEATING LAMBDA SENSOR OF MILD HYBRID ELECTRIC VEHICLE

(71) Applicants: Hyundai Motor Company, Seoul (KR); Kia Motors Corporation, Seoul (KR)

(72) Inventor: Hwa Yong Jang, Hwaseong-si (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 15/828,765

(22) Filed: Dec. 1, 2017

(65) Prior Publication Data

US 2018/0163656 A1    Jun. 14, 2018

(30) Foreign Application Priority Data

Dec. 13, 2016    (KR) .......................... 10-2016-0169827

(51) Int. Cl.
    *F01N 11/00*    (2006.01)
    *F02D 41/14*    (2006.01)
        (Continued)

(52) U.S. Cl.
    CPC ........... *F02D 41/1494* (2013.01); *F01N 9/00* (2013.01); *F01N 11/007* (2013.01);
        (Continued)

(58) Field of Classification Search
    CPC ............... F01N 11/007; F01N 2240/16; F01N 2560/025; F01N 2560/20; F02D 41/123; F02D 41/1494
    See application file for complete search history.

(56) References Cited

U.S. PATENT DOCUMENTS

2013/0110380 A1*  5/2013  Tomimatsu ......... F02D 41/1441
                                                    701/104
2016/0032812 A1*  2/2016  Lee .................... F02D 41/1441
                                                    73/114.73
(Continued)

FOREIGN PATENT DOCUMENTS

JP    2016-112910 A    6/2016
KR    10-2017-0008014 A    1/2017

*Primary Examiner* — Jonathan Matthias
(74) *Attorney, Agent, or Firm* — Morgan, Lewis & Bockius LLP

(57) ABSTRACT

A method and an apparatus for heating a lambda detector of mild hybrid electric vehicle may include determining whether a measured value of the lambda detector is equal to or greater than a first reference value or is equal to or less than a second reference value when an overrun condition is satisfied; determining a first difference value between the measured value of the lambda detector and the first reference value and a second difference value between the measured value and the second reference value when the measured value of the lambda detector is equal to or greater than the first reference value or is equal to or less than the second reference value; determining a heating temperature and time according to the first difference value and the second difference value; and heating the lambda detector according to the determined heating temperature and time when a coasting condition is satisfied.

8 Claims, 4 Drawing Sheets

(51) Int. Cl.
*G01N 27/407* (2006.01)
*F02D 41/12* (2006.01)
*F01N 9/00* (2006.01)

(52) U.S. Cl.
CPC ....... *F02D 41/123* (2013.01); *F02D 41/1454* (2013.01); *G01N 27/407* (2013.01); *F01N 2240/16* (2013.01); *F01N 2560/025* (2013.01); *F01N 2560/20* (2013.01); *F01N 2590/11* (2013.01); *F01N 2900/10* (2013.01); *F01N 2900/12* (2013.01); *F01N 2900/1404* (2013.01); *F02D 2200/501* (2013.01); *F02D 2200/602* (2013.01); *F02D 2200/702* (2013.01)

(56) References Cited

U.S. PATENT DOCUMENTS

2016/0215670 A1    7/2016  Takeuchi et al.
2017/0205326 A1*   7/2017  Kato .................. G01N 27/4067

* cited by examiner

METHOD AND APPARATUS FOR HEATING LAMBDA SENSOR OF MILD HYBRID ELECTRIC VEHICLE

CROSS-REFERENCE(S) TO RELATED APPLICATIONS

The present application claims priority to Korean Patent Application No. 10-2016-0169827, filed on Dec. 13, 2016, the entire contents of which is incorporated herein for all purposes by this reference.

BACKGROUND OF THE INVENTION

Field of the Invention

The present invention relates to a method and an apparatus for heating a lambda detector of a mild hybrid electric vehicle.

Description of Related Art

In general, a hybrid electric vehicle utilizes an internal combustion engine and a battery power source in combination. The hybrid electric vehicle efficiently combines a torque of the internal combustion engine and a torque of a motor.

Hybrid electric vehicles may be subdivided into a hard type and a mild type according to a power sharing ratio between the engine and the motor. In the case of the mild type of hybrid electric vehicle (hereinafter referred to as a mild hybrid electric vehicle), a mild hybrid starter & generator (MHSG) configured to start the engine or generate electricity according to an output of the engine is used instead of an alternator. In the case of the hard type of hybrid electric vehicle, a driving motor configured for generating a driving torque is used in addition to an integrated starter & generator (ISG) configured to start the engine or generate electricity.

The MHSG may assist the torque of the engine according to a plurality of operational states of the vehicle, and may charge a battery (e.g., a 48 V battery) through regenerative braking device. Accordingly, a fuel efficiency of the mild hybrid electric vehicle may be improved.

Energy generated by combusting fuel is converted into mechanical energy to operate the engine. Exhaust gas is generated in the combustion process of the fuel, and harmful materials in the exhaust gas are purified. After that, the exhaust gas is expelled into the atmosphere through an exhaust pipe.

A lambda sensor measuring an oxygen level included in the exhaust gas, is applied to an exhaust system. Lean and/or rich control of the exhaust gas may be performed according to a signal of the lambda sensor. An electrode to measure the oxygen level is internally disposed within the lambda sensor. An electrode of the lambda sensor may be poisoned by siloxane. When the electrode of the lambda sensor is poisoned, a signal of the lambda sensor may deteriorate.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a method and an apparatus for heating a lambda detector of a mild hybrid electric vehicle having advantages of removing a poison of an electrode of the lambda sensor.

A method for heating the lambda detector of the mild hybrid electric vehicle according to an exemplary embodiment of the present invention may include determining whether a measured value of the lambda detector is equal to or greater than a first reference value or is equal to or less than a second reference value when an overrun condition of an engine is satisfied; determining a first difference value between the measured value of the lambda detector and the first reference value and a second difference value between the measured value and the second reference value when the measured value of the lambda detector is equal to or greater than the first reference value or is equal to or less than the second reference value; determining a heating temperature and a heating time according to the first difference value and the second difference value; and heating the lambda detector according to the determined heating temperature and the determined heating time when a coasting condition is satisfied.

The heating temperature and the heating time may be increased as the first difference value or the second difference value is increased.

Satisfaction of the coasting condition may be determined according to a position value of an accelerator pedal, a position value of a brake pedal, a speed of the mild hybrid electric vehicle, and a gradient of a road.

The coasting condition may be satisfied when the position value of the accelerator pedal is a first predetermined position value, the position value of the brake pedal is a second predetermined position value, the speed of the mild hybrid electric vehicle is equal to or greater than a first predetermined value, and the gradient of the road is within a predetermined gradient range.

An apparatus for heating a lambda detector of a mild hybrid electric vehicle according to an exemplary embodiment of the present invention may include: the lambda detector including an electrode measuring an oxygen level included in an exhaust gas and a heater heating the electrode; an accelerator pedal position detector measuring a position value of an accelerator pedal; a brake pedal position detector configured to measure a position value of a brake pedal; a vehicle speed detector configured to measure a speed of the mild hybrid electric vehicle; a gradient detector configured to measure a gradient of a road; and a controller configured to determine whether a measured value of the lambda detector is equal to or greater than a first reference value or is equal to or less than a second reference value when an overrun condition of an engine is satisfied, wherein the controller is configured to determine a first difference value between the measured value of the lambda detector and the first reference value and a second difference value between the measured value and the second reference value when the measured value of the lambda detector is equal to or greater than the first reference value or is equal to or less than the second reference value, determine a heating temperature and a heating time according to the first difference value and the second difference value, and heats the lambda detector according to the determined heating temperature and the determined heating time when a coasting condition is satisfied.

The heating temperature and the heating time may be increased as the first difference value or the second difference value is increased.

The controller may be configured to determine whether the coasting condition is satisfied according to the position value of the accelerator pedal, the position value of the brake pedal, the speed of the mild hybrid electric vehicle, and the gradient of the road.

The coasting condition may be satisfied when the position value of the accelerator pedal is a first predetermined position value, the position value of the brake pedal is a second predetermined position value, the speed of the mild hybrid electric vehicle is equal to or greater than a first predetermined value, and the gradient of the road is within a predetermined gradient range.

According to an exemplary embodiment of the present invention, poison of a lambda detector may be removed, preventing the performance of the lambda detector from deteriorating.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
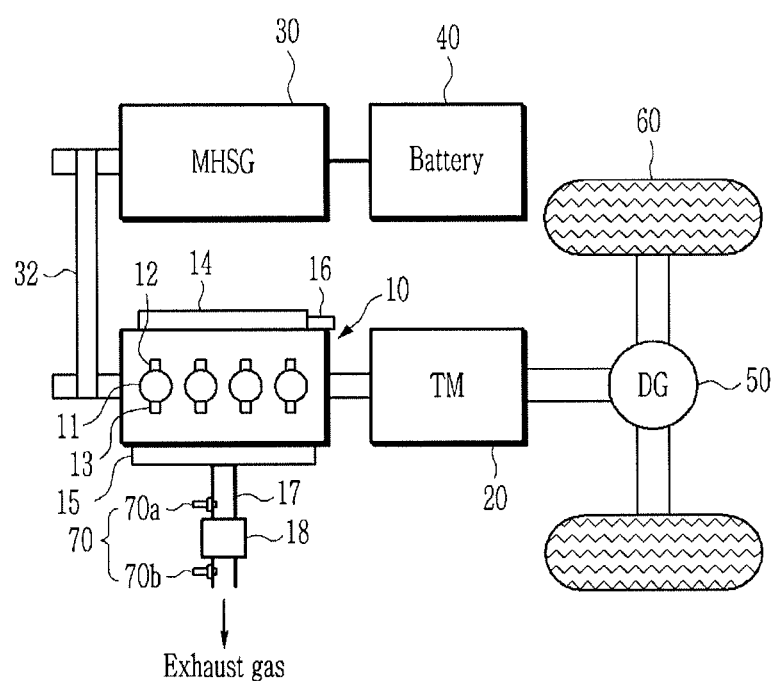
FIG. 1 is a block diagram of a mild hybrid electric vehicle according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particularly intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the other hand, the invention(s) is/are intended to cover not only the exemplary embodiments, but also various alternatives, modifications, equivalents and other embodiments, which may be included within the spirit and scope of the invention as defined by the appended claims.

Elements which are not related with the description are omitted for clearly describing the exemplary embodiments of the present invention.

Since each component in the drawings is arbitrarily illustrated for ease of description, the present invention is not particularly limited to the components illustrated in the drawings.

Figure 2:
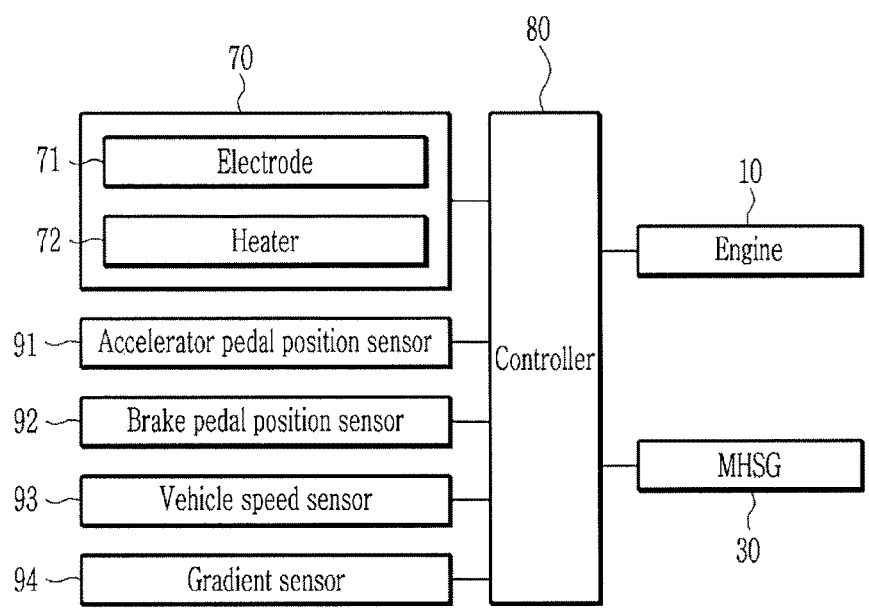
FIG. 2 is a block diagram illustrating an apparatus for heating a lambda detector of a mild hybrid electric vehicle according to an exemplary embodiment of the present invention.

FIG. 1 is a block diagram of a mild hybrid electric vehicle according to an exemplary embodiment of the present invention, and FIG. 2 is a block diagram illustrating an apparatus for heating a lambda detector of a mild hybrid electric vehicle according to an exemplary embodiment of the present invention.

As shown in FIG. 1, the mild hybrid electric vehicle according to an exemplary embodiment of the present invention includes an engine 10, a transmission 20, a mild hybrid starter & generator (MHSG) 30, a battery 40, a differential gear apparatus 50, and wheels 60.

The engine 10 combusts fuel and air to convert chemical energy into mechanical energy.

With reference to a torque transmission of the mild hybrid electric vehicle, a torque generated from the engine 10 is transmitted to an input shaft of the transmission 20, and the torque output from an output shaft of the transmission 20 is transmitted to an axle via the differential gear apparatus 50. The axle rotates the wheels 60 wherein the mild hybrid electric vehicle drives by the torque generated from the engine 10.

The MHSG 30 converts electrical energy into mechanical energy or converts mechanical energy into electrical energy. The MHSG 30 starts the engine 10 or generates electricity according to an output of the engine 10. In addition, the MHSG 30 may assist the torque of the engine 10. The torque of the engine 10 may be used as a main torque, and the torque of the MHSG 30 may be used as an auxiliary torque. The engine 10 and the MHSG 30 may be connected to each other through a belt 32.

The battery 40 may supply electricity to the MHSG 30, and may be charged through electricity recovered by the MHSG 30. The battery 40 may be a 48 V battery. The mild hybrid electric vehicle may further include a low voltage battery DC-DC converter (LDC) converting a voltage supplied from the battery 40 into a low voltage, and a low voltage battery (e.g., a 12 V battery) supplying a low voltage to electrical loads (e.g., a head lamp and an air conditioner).

The engine 10 may include a plurality of combustion chambers 11 into which fuel and air flow, an ignition device 12 igniting the fuel air mixture flowing into the combustion chamber 11, and an injector 13 injecting the fuel. The engine 10 is connected to an intake manifold 14 to receive the air in the combustion chamber 11, and an exhaust gas generated in the combustion process is gathered in an exhaust manifold 15 and is expelled to an external of the vehicle. The injector 13 may be mounted in the combustion chamber 11 or the intake manifold 14.

A throttle valve 16 is disposed on an intake line supplying the air to the intake manifold 14. The flow of air supplied to the intake manifold 14 is controlled according to an opening degree of the throttle valve 16.

An exhaust pipe 17 is connected to the exhaust manifold 15 to expel the exhaust gas to the external of the mild hybrid electric vehicle. A catalyst 18 may be mounted on the exhaust pipe 17 and removes hydrocarbons, carbon monoxide, and nitrogen oxide included in the exhaust gas.

A first lambda detector 70a may be mounted on the exhaust pipe 17 upstream of the catalyst 18. The first lambda detector 70a is configured to measure an oxygen level included in the exhaust gas flowing into the catalyst 18, and transmits a signal corresponding thereto to a controller 80. A measured value by the first lambda detector 70a may be represented as a lambda. The lambda means a ratio of an actual air-fuel ratio to a stoichiometric air-fuel ratio. When the lambda is greater than 1, the air-fuel ratio is considered lean. On the other hand, the air-fuel ratio is considered rich when the lambda is less than 1.

A second lambda detector 70b may be mounted on the exhaust pipe 17 downstream of the catalyst 18. The second lambda detector 70b is configured to measure an oxygen level included in the exhaust gas expelled from the catalyst 18, and transmits a signal corresponding thereto to the controller 80.

A method for heating a lambda detector according to an exemplary embodiment of the present invention may be applied to the first lambda detector 70a and the second lambda detector 70b. Hereinafter, the first lambda detector 70a and the second lambda detector 70b will be referred to as a lambda detector 70.

As shown in FIG. 2, an apparatus for heating a lambda detector of a mild hybrid electric vehicle according to an exemplary embodiment of the present invention may include the lambda detector 70, an accelerator pedal position detector 91, a brake pedal position detector 92, a vehicle speed detector 93, a gradient detector 94, and the controller 80.

The lambda detector 70 includes an electrode 71 and a heater 72. The electrode 71 measures an oxygen level included in the exhaust gas, and the heater 72 heats the electrode 71.

The exhaust gas includes a plurality of materials, and the electrode 71 may be poisoned by siloxane. When the electrode 71 is poisoned, the measured value of the lambda detector 70 deteriorates. When the electrode 71 is poisoned, the controller 80 may be configured to heat the electrode 71 to remove the poison of the electrode 71 using the heater 72.

The accelerator pedal position detector 91 measures a position value of an accelerator pedal, and transmits corresponding a signal to the controller 80. When the accelerator pedal is pushed completely, the position value of the accelerator pedal is 100%, and when the accelerator pedal is not pushed, the position value of the accelerator pedal is 0%.

The brake pedal position detector 92 is configured to measure a position value of a brake pedal, and transmits a corresponding signal to the controller 80. When the brake pedal is completely depressed, the position value of the brake pedal is considered 100%, and when the brake pedal is not depressed, the position value of the brake pedal is considered 0%.

The vehicle speed detector 93 is configured to measure a speed of the mild hybrid electric vehicle, and transmits a corresponding signal to the controller 80.

The gradient detector 94 is configured to measure a gradient of a road, and transmits a corresponding signal to the controller 80.

The controller 80 is configured to control the operations of the engine 10, the MHSG 30, and the heater 72 according to signals of the electrode 71, the accelerator pedal position detector 91, the brake pedal position detector 92, the vehicle speed detector 93, and the gradient detector 94.

The controller 80 may be implemented with one or more processors executed by a predetermined program, and the predetermined program may include a series of commands for performing each step included in a method for controlling an MHSG of a mild hybrid electric vehicle according to an exemplary embodiment of the present invention.

Figure 3:
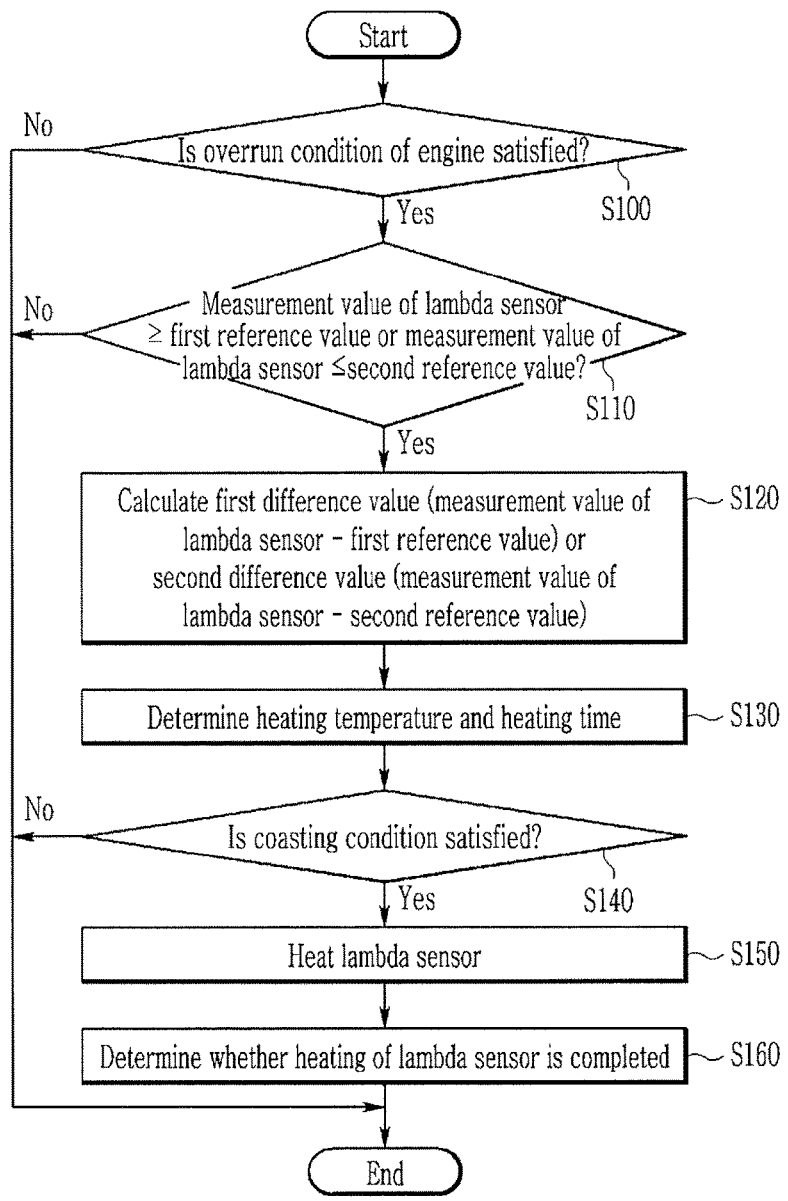
FIG. 3 is a flowchart illustrating a method for heating a lambda detector of a mild hybrid electric vehicle according to an exemplary embodiment of the present invention.
Figure 4:
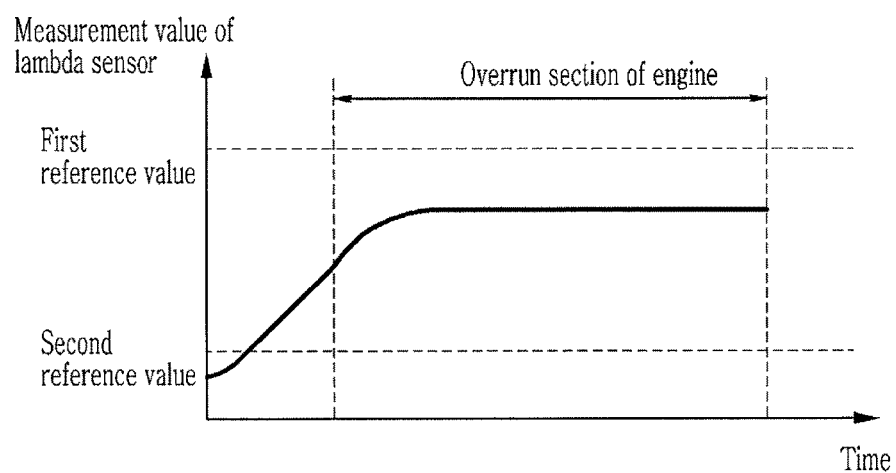
FIG. 4 is a graph for explaining a method for heating a lambda detector of a mild hybrid electric vehicle according to an exemplary embodiment of the present invention.

FIG. 3 is a flowchart illustrating a method for heating a lambda detector of a mild hybrid electric vehicle according to an exemplary embodiment of the present invention, and FIG. 4 is a graph for explaining a method for heating a lambda detector of a mild hybrid electric vehicle according to an exemplary embodiment of the present invention.

Referring to FIG. 3 and FIG. 4, the controller 80 is configured to determine whether an overrun condition of the engine 10 is satisfied (S100). The overrun condition of the engine 10 may be satisfied when the position value of the throttle is 0% while the mild hybrid electric vehicle is traveling. When the overrun condition of the engine 10 is satisfied, fuel is not injected into the engine 10. When a volume or concentration of the exhaust gas is sharply changed, the oxygen level included in the exhaust gas may be also sharply changed. Accordingly, the controller 80 is configured to determine whether the lambda detector 70 is poisoned in an overrun section in which the level of the exhaust gas is constantly maintained.

When the overrun condition of the engine 10 is not satisfied (S100), the controller 80 is configured to end the method for heating the lambda detector 70 of the mild hybrid electric vehicle according to an exemplary embodiment of the present invention.

When the overrun condition of the engine 10 is satisfied (S100), the controller 80 is configured to determine whether the measured value of the lambda detector 70 is equal to or greater than a first reference value or is equal to or less than a second reference value (S110).

When the measured value of the lambda detector 70 is between the first reference value and the second reference value (S110), the controller 80 is configured to end the method for heating the lambda detector 70 according to an exemplary embodiment of the present invention. In the present case, the controller 80 may determine that lambda detector 70 is in a normal state.

When the measured value of the lambda detector 70 is equal to or greater than the first reference value or is equal to or less than the second reference value at step S110, the controller 80 may determine that the lambda detector 70 is poisoned. The first reference value and the second reference value may be predetermined by a person of ordinary skill in the art through experimentation.

When the measured value of the lambda detector 70 is equal to or greater than the first reference value, the controller 80 is configured to determine a first difference value between the measured value of the lambda detector 70 and the first reference value (S120). In addition, when the measured value of the lambda detector 70 is equal to or less than the second reference value, the controller 80 is configured to determine a difference value between the measured value of the lambda detector 70 and the second reference value.

The controller 80 is configured to determine a heating temperature and a heating time according to the first difference value or the second difference value (S130). As the first difference value or the second difference value is increased, the heating temperature and the heating time may be increased.

The controller 80 is configured to determine whether a coasting condition is satisfied (S140). The controller 80 may be configured to determine whether the coasting condition is satisfied according to the position value of the throttle, the position value of the brake pedal, the speed of the mild hybrid electric vehicle, and the gradient of the road. For example, the coasting condition may be satisfied when the position value of the throttle is a first predetermined position value (e.g., 0%), the position value of the brake pedal is a second predetermined position value (e.g., 0%), the speed of the mild hybrid electric vehicle is equal to or greater than a first predetermined speed (e.g., 30 KPH), and the gradient of the road is within a predetermined gradient range (e.g., between −4% and 4%).

When the coasting condition is satisfied (S140), the controller 80 is configured to heat the lambda detector 70 according to the determined heating temperature and the determined heating time (S150). In a state in which the mild hybrid electric vehicle is coasting, fuel is not injected into the engine 10. Accordingly, when the lambda detector 70 is heated, the exhaust gas expelled from the engine 10 is not influenced by the heating. Therefore, poison of the lambda detector 70 may be removed.

The controller 80 is configured to determine whether the lambda detector 70 is thoroughly heated (S160). While the lambda detector 70 is heated according to the determined heating time, a release condition of coasting may be satisfied and the lambda detector 70 may not be thoroughly heated. In the present case, when a next coasting condition satisfied, the lambda detector 70 may be additionally heated for an insufficient heating time. The controller 80 may be configured to determine whether the release condition of coasting is satisfied according to the position value of the accelerator pedal, the position value of the brake pedal, the speed of the mild hybrid electric vehicle, and the gradient of the road. For example, the release condition of coasting may be satisfied when the position value of the accelerator pedal is greater than the first predetermined position value, the position value of the brake pedal is greater than the second predetermined position value, the speed of the mild hybrid electric vehicle is equal to or less than a second predetermined speed (e.g., 25 kph), or the gradient of the road is outside of the predetermined gradient range.

As described above, according to an exemplary embodiment of the present invention, the poison of the lambda detector 70 may be removed, preventing the performance of the lambda detector 70 from deteriorating.

For convenience in explanation and accurate definition in the appended claims, the terms "upper", "lower", "up", "down", "upwards", "downwards", "internal", "outer", "inside", "outside", "inwardly", "outwardly", "internal", "external", "front", "rear", "back", "forwards", and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described to explain certain principles of the invention and their practical application, to enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method for heating a lambda detector of a mild hybrid electric vehicle, the method comprising:
   determining whether a measured value of the lambda detector is equal to or greater than a first reference value or is equal to or less than a second reference value when an overrun condition of an engine is satisfied;
   determining a first difference value between the measured value of the lambda detector and the first reference value and a second difference value between the measured value and the second reference value when the measured value of the lambda detector is equal to or greater than the first reference value or is equal to or less than the second reference value;
   determining a heating temperature and a heating time according to the first difference value and the second difference value; and
   heating the lambda detector according to the determined heating temperature and the determined heating time when a coasting condition is satisfied.

2. The method of claim 1, wherein the heating temperature and the heating time are increased as the first difference value or the second difference value is increased.

3. The method of claim 1, wherein whether the coasting condition is satisfied is determined according to a position value of an accelerator pedal, a position value of a brake pedal, a speed of the mild hybrid electric vehicle, and a gradient of a road.

4. The method of claim 3, wherein the coasting condition is satisfied when the position value of the accelerator pedal is a first predetermined position value, the position value of the brake pedal is a second predetermined position value, the speed of the mild hybrid electric vehicle is equal to or greater than a first predetermined value, and the gradient of the road is within a predetermined gradient range.

5. An apparatus for heating a lambda detector of a mild hybrid electric vehicle, the apparatus comprising:
   the lambda detector including an electrode measuring an oxygen level included in an exhaust gas and a heater heating the electrode;
   an accelerator pedal position detector measuring a position value of an accelerator pedal;
   a brake pedal position detector configured to measure a position value of a brake pedal;
   a vehicle speed detector configured to measure a speed of the mild hybrid electric vehicle;
   a gradient detector configured to measure a gradient of a road; and
   a controller configured to determine whether a measured value of the lambda detector is equal to or greater than a first reference value or is equal to or less than a second reference value when an overrun condition of an engine is satisfied,
   wherein the controller is configured to determine a first difference value between the measured value of the lambda detector and the first reference value and a second difference value between the measured value and the second reference value when the measured value of the lambda detector is equal to or greater than the first reference value or is equal to or less than the second reference value,
   to determine a heating temperature and a heating time according to the first difference value and the second difference value, and
   to heat the lambda detector according to the determined heating temperature and the determined heating time when a coasting condition is satisfied.

6. The apparatus of claim 5, wherein the heating temperature and the heating time are increased as the first difference value or the second difference value increases.

7. The apparatus of claim 5, wherein the controller is configured to determine whether the coasting condition is satisfied according to the position value of the accelerator pedal, the position value of the brake pedal, the speed of the mild hybrid electric vehicle, and the gradient of the road.

8. The apparatus of claim 7, wherein the coasting condition is satisfied when the position value of the accelerator pedal is a first predetermined position value, the position value of the brake pedal is a second predetermined position value, the speed of the mild hybrid electric vehicle is equal to or greater than a first predetermined value, and the gradient of the road is within a predetermined gradient range.

* * * * *